US 6,669,727 B1

(12) United States Patent
Young

(10) Patent No.: US 6,669,727 B1
(45) Date of Patent: Dec. 30, 2003

(54) PROSTHETIC EYE WITH POLARIZED DILATING PUPIL AND COOPERATING POLARIZED EYEGLASS LENS

(76) Inventor: Steven R. Young, 411 30th St., Suite 512, Oakland, CA (US) 94609

( * ) Notice: Subject to any disclaimer, the term of this patent is extended or adjusted under 35 U.S.C. 154(b) by 0 days.

(21) Appl. No.: 10/162,312

(22) Filed: Jun. 3, 2002

Related U.S. Application Data

(60) Provisional application No. 60/295,227, filed on Jun. 1, 2001.

(51) Int. Cl.[7] ............................................... A61F 2/14
(52) U.S. Cl. ..................................................... 623/6.64
(58) Field of Search .............................. 623/4.1, 6.64, 623/6.35, FOR 103

(56) References Cited

U.S. PATENT DOCUMENTS

| | | | |
|---|---|---|---|
| 5,026,392 A | | 6/1991 | Gordon |
| 5,044,743 A | * | 9/1991 | Ting ........................ 351/159 X |
| 5,061,279 A | | 10/1991 | Friel |
| 5,139,518 A | | 8/1992 | White |
| 5,326,346 A | | 7/1994 | Cortes |
| 6,139,577 A | | 10/2000 | Schleipman et al. |

FOREIGN PATENT DOCUMENTS

| | | | | |
|---|---|---|---|---|
| GB | 15938 | * | 6/1894 | ........ 623/FOR 103 |
| RU | 1146037 A | * | 3/1985 | ............. A61F/2/14 |

* cited by examiner

*Primary Examiner*—David H. Willse
(74) *Attorney, Agent, or Firm*—Carol D. Titus; Gregory Smith & Associates

(57) ABSTRACT

A prosthetic eye and a coordinating pair of glasses simulate dilation of the pupil of a normal eye. The prosthetic eye has a white scleral portion with a simulated iris is painted on the front. A polarized disc is located at the center of the iris. The polarized disc is placed on the horizontal transmitting axis. The center of the polarized disc is darkened with paint to simulate a pupil having a fairly small diameter. The back of the polarized disc is painted to blend with the iris or simulate the collarette of the eye. Over the top of the polarized disc and iris is a dome of material simulating the cornea of the eye. The prosthetic eye is used in conjunction with the special pair of eyeglasses having a lens formed of linearly polarizing material with the transmitting axis in the vertical plane. When the eyeglasses are used, it makes the pupil appear to dilate because it causes the entire disc to blacken when viewed through the polarized lens. Conversely, removal of the glasses causes it to lighten, showing the details painted on the back of the disc, thereby making the pupil appear smaller in diameter.

15 Claims, 3 Drawing Sheets

US 6,669,727 B1

PROSTHETIC EYE WITH POLARIZED DILATING PUPIL AND COOPERATING POLARIZED EYEGLASS LENS

CROSS-REFERENCE TO OTHER APPLICATIONS

This application claims the benefit of U.S. Provisional Patent Application No. 60/295,227, filed Jun. 1, 2001, which is hereby incorporated by reference in its entirety.

FIELD OF INVENTION

The present invention relates generally to prosthetic eyes. More particularly, it relates to a prosthetic eye with a pupil that can dilate when used with a polarized lens.

BACKGROUND OF THE INVENTION

After injury or disease, a patient may need to have his or her natural eye removed. There are many ocular prosthetic devices that simulate the appearance of a natural eye and attempt to faithfully reproduce the physical features of the natural eye. Often such prosthetic eyes have a simulated iris of a color and pattern so as to match the complementary natural eye and a simulated pupil. The iris image is produced on a white prosthetic shell adapted to be covered with a clear medium. The simulated pupil is of a fixed size and does not react to light intensity, thereby detracting from the appearance of a natural eye. Attempts have been made to simulate a pupil that adjusts to light level so as to provide an appearance of pupil dilation and contraction in response to ambient light. However, these are often complicated, and therefore expensive devices, and may require frequent maintenance or replacement to maintain their desired appearance.

SUMMARY OF INVENTION

The present invention takes the form of a prosthetic eye and a coordinating pair of glasses. The prosthetic eye is formed of a material such as polymethyl-methacrylate and has a globular scleral portion colored white to simulate a human eye. In the place of the normal iris of the eye, a simulated iris is painted on the front of the scleral portion to match the user's natural eye color. A polarized disc is located at the center of the iris. The polarized disc is placed on the horizontal transmitting axis (180 degrees). The center of the front surface of the polarized disc is darkened with paint to simulate a pupil having a fairly small diameter. The back of the polarized disc is painted to blend with the iris or simulate the collarette of the eye. Over the top of the polarized disc and iris is a dome of material simulating the cornea of the eye.

The polarized disc in the prosthetic eye is used in conjunction with the special application of a polarized lens, thereby making the pupil of the eye prosthesis appear to dilate because it causes the entire disc to blacken when viewed through the polarized lens. The lens that is needed to "dilate" the pupil is formed of linearly polarizing material that has been incorporated into the patient's eyeglasses with the transmitting axis in the vertical (90 degree) plane. Wearing the eyeglasses creates the interference between the two polarized lenses, thereby creating a larger darkened area simulating dilation of the pupil. Conversely, removal of the glasses causes it to lighten, showing the details painted on the back of the disc, thereby making the pupil appear smaller in diameter.

DETAILED DESCRIPTION OF THE INVENTION

Figure 1:
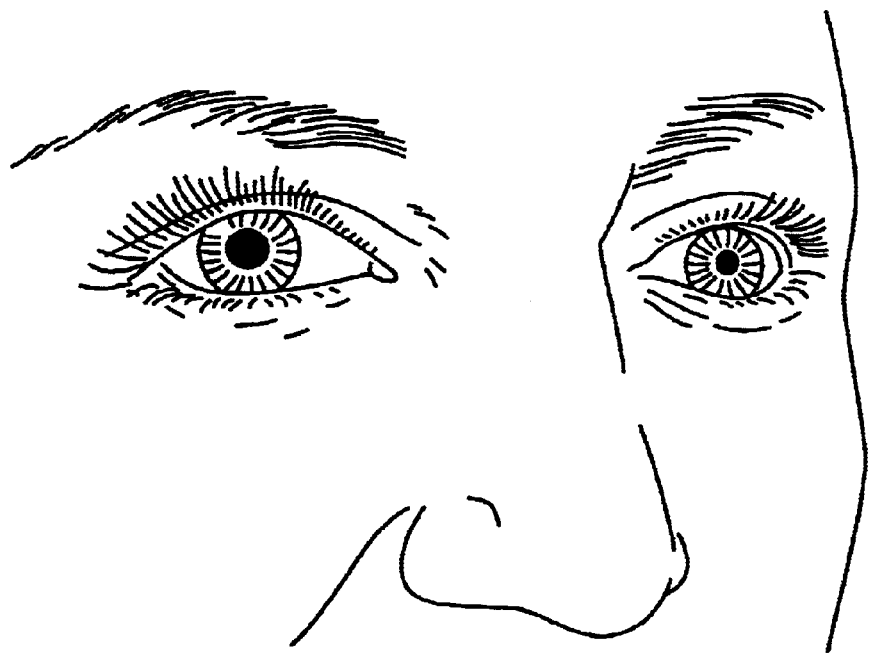
FIG. 1 shows a person in a darkened environment with a prior art prosthetic eye in their left eye socket.

FIG. 1 shows a person in a darkened environment with a prior art prosthetic eye in their left eye socket. The pupil on the left eye is much smaller than the pupil on the right eye.

The present invention, as seen in FIGS. 2–6, is formed of two main parts: a prosthetic eye 10 and pair of glasses 50. The prosthetic eye 10 has a globular scleral portion 12 colored white to simulate a human eye. In the place of the normal iris of the eye, a simulated iris 14 is painted on the front of the scleral portion 12 to match the user's natural eye color. A polarized disc 16 is located at the center of the simulated iris 14. The center of the front surface 18 of the polarized disc 16 is darkened with paint to simulate a pupil 20 having a fairly small diameter. The back of the polarized disc 16 is painted to blend with the iris 14 or simulate the collarette of the eye. Over the top of the polarized disc 16 and iris 14 is a dome 22 of material simulating the cornea of the eye.

Figure 2:
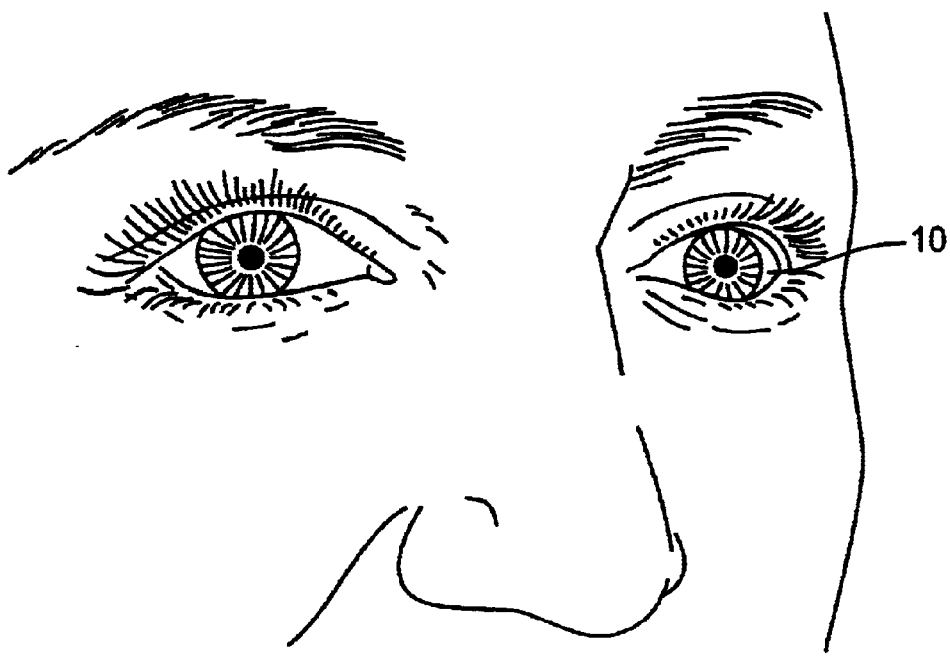
FIG. 2 is a person in a bright environment having a prosthetic eye of the present invention in their left eye socket.

FIG. 2 is a person in a bright environment having a prosthetic eye 10 of the present invention in their left eye socket. As shown, both pupils are contracted to a smaller diameter.

Figure 3:
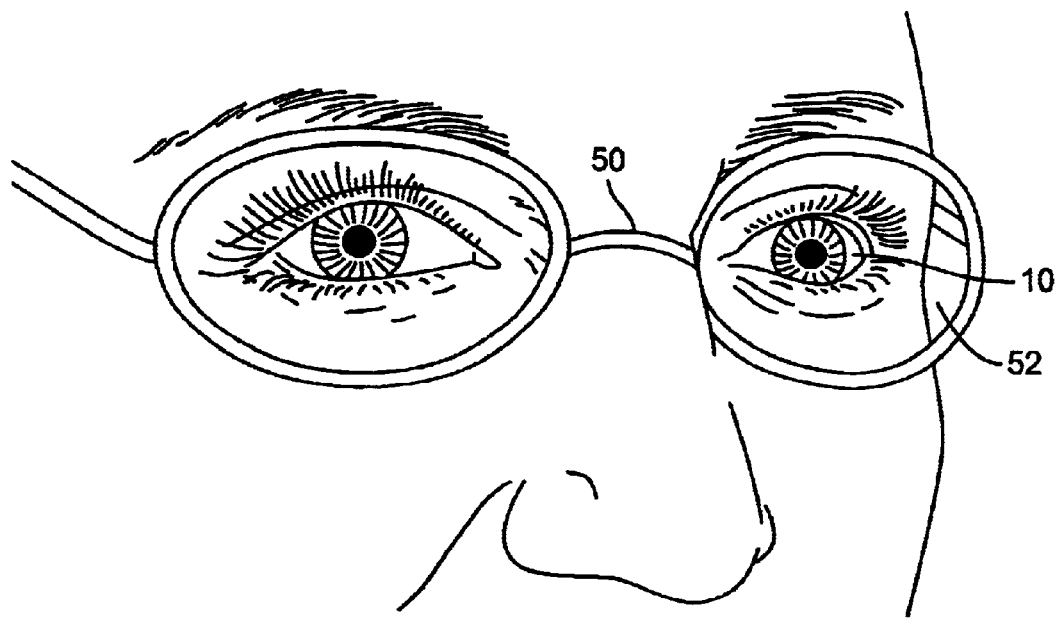
FIG. 3 is a person in a dim environment having a prosthetic eye of the present invention worn with a pair of special glasses.

FIG. 3 is the same configuration as FIG. 2 only the person is now in a dim environment and puts on a pair of special glasses 50. The pupil in the normal eye is dilated and therefore larger. In the prosthetic eye 10, since the direction of the polarization of the polarized disc 16 and the polarized lens 52 of the glasses 50 are 90 degrees from one another, the outer portion of the polarized disc 16 is darkened, thereby simulating a dilated (larger diameter) pupil. When the glasses 50 are removed from in front of the prosthesis 10, the pupil size appears to be smaller (as in FIG. 2), because the polarized disc 16 lightens so that details painted on the back of the disc 16, the additional painted iris or collarette 24, become visible, while the "contracted" pupil 20 painted on the front of the polarized disc 16 remains darkened.

Figure 4:
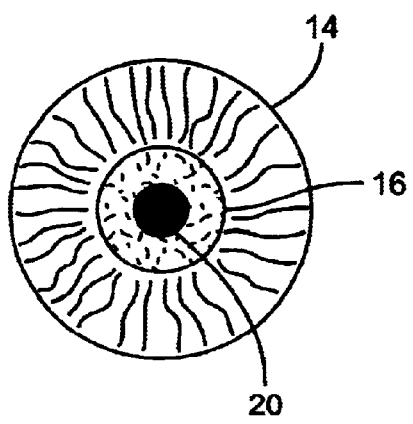
FIG. 4 is a close up view of the iris and pupil of the prosthetic eye.
Figure 5:
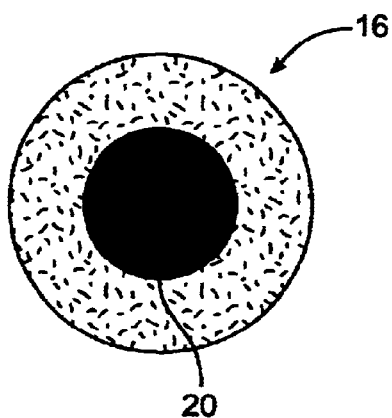
FIG. 5 is a close up of the polarized disc that forms the pupil.
Figure 6:
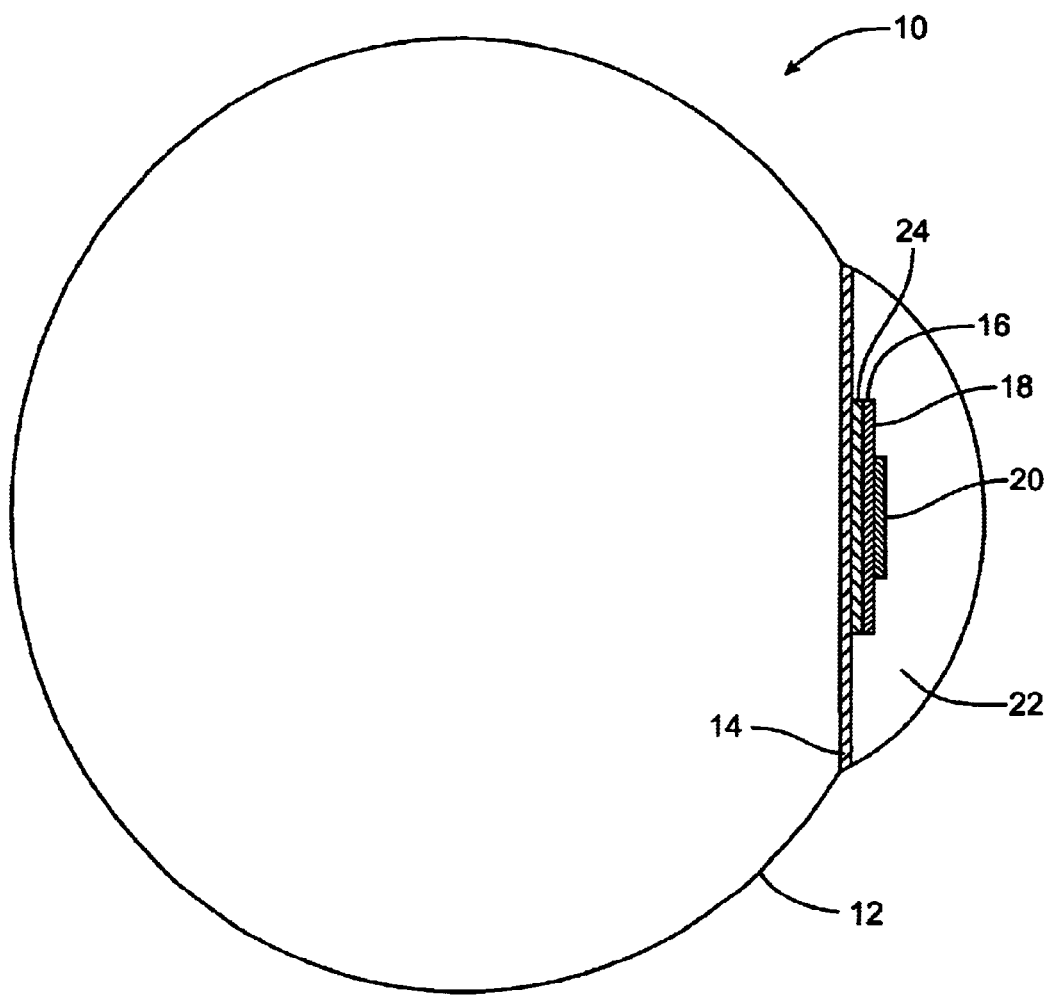
FIG. 6 is a cross-sectional view of the prosthetic eye.

FIG. 4 is a close up view of the iris 14 and pupil 20 of the prosthetic eye 10. FIG. 5 is a close up of the polarized disc 16 that forms the pupil 20. FIG. 6 is a cross-sectional view of the prosthetic eye 10. The polarized disc 16, which is incorporated into a prosthetic eye 10, is the size of a dilated pupil and is used in conjunction with the special application of a polarized lens 52 in eyeglasses 50 to make the pupil 20 of the eye prosthesis 10 appear to dilate because it causes the entire polarized disc 16 to blacken when viewed through the polarized lens 52. Conversely, removal of the eyeglasses 50 allows an observer to see through the outer part of the disc 16, showing the details 24 painted on the back of the disc 16.

Polarized Pupil Disc Description

A polymethylmethacrylate (PMMA), or other suitable material, artificial eye 10 is made in the usual way to the point where the flat painted surface of the iris 14 is exposed.

A pupil disc 16 is then selected and striations or glazes 24 are painted on the back of the disc 16 to match the natural companion eye, keeping in mind the influence on hue that the color of the pupil disc 16 itself will have on the final color outcome. For example, on a brown pupil disc 16, the use of a heavy creamy mixture of white and cadmium yellow deep striated on the back of the disc 16 will produce a good character and medium brown color. On a blue-grey pupil disc, if the color desired is a dark warm grey, a much brighter orange or red must be glazed or painted on the back of the disc because it will be muted and neutralized by the blue-grey of the pupil disc. The disc 16 can be set on the iris 14 with a large drop of water, a painting lens or a painting shell over it to check color. Alternately, another type of simulated iris may be used, such as a print or photo of the companion eye mounted on the scleral portion 12.

After the pupil disc 16 is glazed or painted, it should be coated with 2 or 3 layers of monopoly and allowed to dry. The front surface of the iris 14 of the prosthesis 10 should also be allowed to dry well. Then, the pupil disc 16 can be glued with any suitable glue, such as cyanoacrylate, or attached with a thin glaze of monomer-polymer put on the disc 16. It should immediately be set on the iris 14 carefully so it doesn't move around. It is suggested that the disc 16 be placed precisely where it needs to be with tweezers and tapped gently to seat it. The pupil disc 16 is placed on the horizontal transmitting axis (180 degrees). The glue is then allowed to dry, the edge of the pupil disc 16 can be colored to blend in with the collarette. Paint applied to the front 18 of the disc 16 will not allow good extinction when the special glasses are placed in front of the eye 10, so great care must be taken to preserve the outer portion of the front 18 of the disc 16 paint-free in order to allow the pupil disc 16 to "dilate" clearly.

A small pupil 20 is painted or affixed to the front 18 of the disc 16. If preferred, the pupil 20 may be painted or placed to the back of the disc 16. An observer would view the pupil 20 through the disc 16 when the eyeglasses 50 were not in place. When the eyeglasses 50 were used, the entire disc 16 would be blackened. Alternately, if a small hole was pre-punched for the desired size and location of the small pupil 20 before incorporating the disc 16 onto the artificial eye, the bottom of the hole, created by the scleral portion 12, is painted black at this time.

Optimally, after the entire painted surface is allowed to dry, the prosthesis 10 is capped with clear plastic in the usual way, polished and delivered.

Eyeglasses Lens Description

The lens 52 that is needed to "dilate" the pupil disc 16 is formed of linearly polarizing material that has been incorporated into the patient's eyeglasses 50 with the transmitting axis in the vertical (90 degree) plane. This is a difference from the sunglass type polarized lenses now on the market, because typical sunglass lenses are arranged with their transmitting axes on the horizontal plane (180 degrees) to decrease the glare caused by reflected light. Also, since it is not desirable for the pupil to "dilate" in bright light, it is important that current sunglasses do not "activate" the pupil disc 16. In most cases, the second lens, which is over the patient's normal eye, will be of the same material to properly color match the other lens 52. The orientation of the polarization may be the same or different in the two lenses. In other embodiments, the second lens may not be polarized. In the non-polarized cases, the color of the second lens will have to be carefully matched to the color of the dilation lens 52. The special glasses 50 described herein will be worn only in dim light (where the pupil disc 16 needs to be dilated).

In alternate embodiments, the axis of the disc 16 and lens 52 could be rotated as long as the axes remain at 90 degrees to one another.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

I claim:

1. A prosthetic eye, comprising:
   a globular scleral portion having a front surface and a top,
   a simulated iris on said front surface,
   a polarized disc placed on said front surface, said polarized disc oriented with a selected transmitting axis,
   and a simulated pupil having a first diameter located on said polarized disc.

2. The prosthetic eye of claim 1, wherein said selected transmitting axis is generally horizontal.

3. The prosthetic eye of claim 2, used in combination with a pair of glasses, said pair of glasses including:
   a first polarized lens, configured to be placed over said prosthetic eye, said first polarized lens oriented to have a generally vertical transmitting axis when placed over the prosthetic eye,
   a second lens,
   and a frame holding said first and second lenses.

4. The prosthetic eye of claim 1, wherein said globular scleral portion is formed of polymethylmethacrylate.

5. The prosthetic eye of claim 1, wherein said simulated iris is formed of paint placed on said front surface of said scleral portion.

6. The prosthetic eye of claim 1, wherein additional simulated iris is formed of paint located on a back surface of said polarized disc.

7. The prosthetic eye of claim 1, wherein said additional simulated iris is color selected to match said simulated iris on said scleral portion when said additional simulated iris is viewed through said polarized disc.

8. The prosthetic eye of claim 1, wherein said simulated pupil is formed of paint located on a front surface of said polarized disc.

9. The prosthetic eye of claim 1, used in combination with a pair of glasses, said pair of glasses including:
   a first polarized lens, configured to be placed over said prosthetic eye, said first polarized lens oriented to have a transmitting axis perpendicular to said selected axis when placed over the prosthetic eye,
   a second lens,
   and a frame holding said first and second lenses.

10. The combination of claim 9, wherein said second lens is formed of a polarized material.

11. In combination:
   a prosthetic eye, including:
      a globular scleral portion formed of polymethylmethacrylate and having a front surface and a top,
      a simulated iris painted on said front surface,
      a polarized disc placed on said front surface, said polarized disc oriented with a generally horizontal transmitting axis,
      additional simulated iris painted on a back surface of said polarized disc, said additional simulated iris being color selected to match said simulated iris on said scleral portion when said additional simulated iris is viewed through said polarized disc, and a simulated pupil painted on a front of said polarized disc and having a first diameter,
and a pair of glasses, including:
  a first polarized lens, configured to be placed over said prosthetic eye, said first polarized lens oriented to have a generally vertical transmitting axis, thereby creating a darkened area around said simulated pupil when said first polarized lens is placed over the prosthetic eye,
  a second lens,
  and a frame holding said first and second lenses.

12. A method of making a dilating prosthetic eye, comprising the steps of:
  (a) forming a globular scleral portion;
  (b) painting a simulated iris on a flat front surface of said scleral portion;
  (c) painting additional simulated iris on a back surface of a polarized disc;
  (d) orienting said polarized disc to have a selected transmitting axis;
  (e) attaching said polarized disc to said flat front surface of said scleral portion;
  (f) and forming a simulated pupil on said polarized disc.

13. The method of claim 12, wherein said simulated pupil is affixed to a front surface of said polarized disc.

14. The method of claim 12, wherein said additional simulated iris is color selected to match said simulated iris on said flat front surface when said additional simulated iris is viewed through said polarized disc.

15. The method of claim 12, wherein said polarized disc is oriented to have a generally horizontal transmitting axis.

* * * * *